(12) United States Patent
Harper et al.

(10) Patent No.: US 11,389,229 B2
(45) Date of Patent: Jul. 19, 2022

(54) SURGICAL FORCEPS CAPABLE OF ADJUSTING SEALING PRESSURE BASED ON VESSEL SIZE

(71) Applicant: COVIDIEN LP, Mansfield, MA (US)

(72) Inventors: Jennifer S. Harper, Westminster, CO (US); J. Bruce Dunne, Longmont, CO (US)

(73) Assignee: Covidien LP, Mansfield, MA (US)

( * ) Notice: Subject to any disclaimer, the term of this patent is extended or adjusted under 35 U.S.C. 154(b) by 368 days.

(21) Appl. No.: 16/430,474

(22) Filed: Jun. 4, 2019

(65) Prior Publication Data

US 2019/0282296 A1 Sep. 19, 2019

Related U.S. Application Data

(63) Continuation of application No. 14/747,135, filed on Jun. 23, 2015, now Pat. No. 10,335,226, which is a
(Continued)

(51) Int. Cl.
*A61B 18/14* (2006.01)
*A61B 5/0538* (2021.01)
(Continued)

(52) U.S. Cl.
CPC ........ *A61B 18/1445* (2013.01); *A61B 5/0538* (2013.01); *A61B 5/1076* (2013.01);
(Continued)

(58) Field of Classification Search
CPC .............. A61B 18/1445; A61B 5/0538; A61B 2090/064; A61B 2090/065
See application file for complete search history.

(56) References Cited

U.S. PATENT DOCUMENTS 5,618,294 A 4/1997 Aust et al.
5,693,051 A 12/1997 Schulze et al.
(Continued)

FOREIGN PATENT DOCUMENTS

DE 2415263 A1 10/1975
DE 02514501 A1 10/1976
(Continued)

OTHER PUBLICATIONS

U.S. Appl. No. 12/565,281, filed Sep. 23, 2009.
(Continued)

*Primary Examiner* — Daniel L Cerioni
*Assistant Examiner* — Raymond P Dulman
(74) *Attorney, Agent, or Firm* — Carter, Deluca & Farrell LLP (57) ABSTRACT

A surgical forceps includes a housing having one or more shafts attached thereto and an end effector assembly disposed at a distal end thereof. The end effector assembly includes first and second jaw members disposed in opposing relation relative to one another. At least one jaw member is moveable from an open position to a closed position for grasping tissue therebetween. The jaw members include at least one sensing component that determines an output of one or both of cross-sectional diameter and composition of tissue disposed between the jaw members. A processing component is configured to receive the output and determine a seal pressure for adequately sealing tissue disposed between the jaw members based upon the output. A regulating component regulates the movement of the jaw members between the first and second positions such that the determined seal pressure is applied to tissue disposed therebetween.

17 Claims, 6 Drawing Sheets

Related U.S. Application Data continuation of application No. 12/619,100, filed on Nov. 16, 2009, now Pat. No. 9,060,798.

(51) Int. Cl.
*A61B 5/107* (2006.01)
*A61B 5/00* (2006.01)
*A61B 90/00* (2016.01)
*A61B 17/28* (2006.01)
*A61B 18/00* (2006.01)

(52) U.S. Cl.
CPC ........ *A61B 5/4869* (2013.01); *A61B 17/2812* (2013.01); *A61B 90/06* (2016.02); *A61B 18/14* (2013.01); *A61B 2018/00053* (2013.01); *A61B 2018/0063* (2013.01); *A61B 2090/064* (2016.02); *A61B 2090/065* (2016.02)

(56) References Cited

U.S. PATENT DOCUMENTS

| | | |
|---|---|---|
| 5,791,231 A | 8/1998 | Cohn et al. |
| 5,807,393 A | 9/1998 | Williamson, IV et al. |
| 5,810,881 A | 9/1998 | Hoskin et al. |
| 5,876,401 A | 3/1999 | Schulze et al. |
| 6,039,733 A | 3/2000 | Buysse et al. |
| 6,050,996 A | 4/2000 | Schmaltz et al. |
| 6,083,150 A | 7/2000 | Aznoian et al. |
| 6,083,223 A | 7/2000 | Baker |
| 6,096,037 A | 8/2000 | Mulier et al. |
| 6,113,598 A | 9/2000 | Baker |
| 6,179,834 B1 | 1/2001 | Buysse et al. |
| 6,440,130 B1 | 8/2002 | Mulier et al. |
| 6,610,060 B2 | 8/2003 | Mulier et al. |
| 6,613,048 B2 | 9/2003 | Mulier et al. |
| 6,755,338 B2 | 6/2004 | Hahnen et al. |
| 6,755,824 B2 | 6/2004 | Jain et al. |
| 6,858,028 B2 | 2/2005 | Mulier et al. |
| 6,926,716 B2 | 8/2005 | Baker et al. |
| 6,929,644 B2 | 8/2005 | Truckai et al. |
| 7,001,408 B2 | 2/2006 | Knodel et al. |
| 7,025,763 B2 | 4/2006 | Karasawa et al. |
| 7,113,831 B2 | 9/2006 | Hooven |
| 7,115,139 B2 | 10/2006 | McClurken et al. |
| 9,060,798 B2 | 6/2015 | Harper et al. |
| 10,335,226 B2 | 7/2019 | Harper et al. |
| 2003/0018332 A1* | 1/2003 | Schmaltz ........... A61B 18/1445 606/51 |
| 2005/0107824 A1 | 5/2005 | Hillstead et al. |
| 2006/0129146 A1 | 6/2006 | Dycus et al. |
| 2006/0259054 A1 | 11/2006 | Masuda et al. |
| 2007/0142834 A1 | 6/2007 | Dumbauld |
| 2007/0173804 A1 | 7/2007 | Wham et al. |
| 2007/0173813 A1 | 7/2007 | Odom |
| 2008/0009860 A1 | 1/2008 | Odom |
| 2008/0039831 A1 | 2/2008 | Odom et al. |
| 2008/0167644 A1 | 7/2008 | Shelton et al. |
| 2008/0294041 A1* | 11/2008 | Kassab ............... A61B 5/02007 600/433 |
| 2008/0300580 A1 | 12/2008 | Shelton, IV et al. |
| 2009/0012556 A1 | 1/2009 | Boudreaux et al. |
| 2009/0138006 A1 | 5/2009 | Bales et al. |
| 2009/0240246 A1* | 9/2009 | Deville ............... A61B 18/1445 606/33 |
| 2009/0248022 A1* | 10/2009 | Falkenstein ........ A61B 18/1442 606/51 |
| 2009/0299365 A1* | 12/2009 | Stewart ............... A61B 18/1445 606/41 |

FOREIGN PATENT DOCUMENTS

| | | |
|---|---|---|
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| EP | 1159926 A2 | 3/2003 |
| EP | 1810628 A1 | 7/2007 |
| JP | 61501068 A | 5/1986 |
| JP | 65502328 | 3/1992 |
| JP | 55106 | 1/1993 |
| JP | 0540112 A | 2/1993 |
| JP | 06343644 | 12/1994 |
| JP | 07265328 | 10/1995 |
| JP | 08056955 | 3/1996 |
| JP | 08252263 A | 10/1996 |
| JP | 09010223 | 1/1997 |
| JP | 11070124 A | 3/1999 |
| JP | 11244298 | 9/1999 |
| JP | 2000102545 A | 4/2000 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| SU | 401367 A1 | 10/1973 |
| WO | 9710764 A1 | 3/1997 |
| WO | 0036986 A1 | 6/2000 |
| WO | 0154604 A1 | 8/2001 |
| WO | 2005110264 A2 | 4/2006 |

OTHER PUBLICATIONS

U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Intl Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Intl Search Report EP 05017281.6 dated Nov. 24, 2005.
int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report-extended-EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.

(56) References Cited

OTHER PUBLICATIONS

Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended-EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
International Search Report EP10191320 dated Feb. 15, 2011.
U.S. Appl. No. 12/176,679, filed Jul. 21, 2008.
U.S. Appl. No. 12/192,170, filed Aug. 15, 2008.
U.S. Appl. No. 12/192,189, filed Aug. 15, 2008.
U.S. Appl. No. 12/192,243, filed Aug. 15, 2008.
U.S. Appl. No. 12/195,624, filed Aug. 21, 2008.
U.S. Appl. No. 12/200,154, filed Aug. 28, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/204,976, filed Sep. 5, 2008.
U.S. Appl. No. 12/210,598, filed Sep. 15, 2008.
U.S. Appl. No. 12/211,205, filed Sep. 16, 2008.
U.S. Appl. No. 12/233,157, filed Sep. 18, 2008.
U.S. Appl. No. 12/236,666, filed Sep. 24, 2008.
U.S. Appl. No. 12/237,515, filed Sep. 25, 2008.
U.S. Appl. No. 12/237,556, filed Sep. 25, 2008.
U.S. Appl. No. 12/237,582, filed Sep. 25, 2008.
U.S. Appl. No. 12/244,873, filed Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/363,086, filed Jan. 30, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

SURGICAL FORCEPS CAPABLE OF ADJUSTING SEALING PRESSURE BASED ON VESSEL SIZE

CROSS-REFERENCE TO RELATED APPLICATIONS

This application is a continuation application of U.S. patent application Ser. No. 14/747,135, filed on Jun. 23, 2015, which is a continuation application of U.S. patent application Ser. No. 12/619,100, filed on Nov. 16, 2009, the entire contents of each of which are hereby incorporated herein by reference.

BACKGROUND

Technical Field

The present disclosure relates to a surgical forceps, and more particularly, to a surgical forceps and method for determining and applying a minimum seal pressure to tissue based upon tissue diameter and/or composition.

Background of Related Art

As an alternative to open forceps for use with open surgical procedures, modern surgeons use endoscopic or laparoscopic instruments for remotely accessing organs through smaller, puncture-like incisions. More recently, Natural Orifice Translumenal Endoscopic Surgery (NOTES) procedures have been developed, for example, to access the abdominal cavity via the mouth, for scar-less surgery. Much like laparoscopy, NOTES is beneficial to patients in that it reduces healing time. However, while these minimally invasive surgical procedures are advantageous in many respects, the reduced access area presents new problems for surgical instrument design. For example, achieving a high seal pressure with a surgical forceps becomes increasingly more difficult as the size of the jaw members decreases. Accordingly, determining a minimum seal pressure needed to effectively seal tissue having a given diameter would be helpful in designing surgical instrument for use in laparoscopic or NOTES procedures.

Further, the proper seal pressures, or seal pressure ranges, required to effectively seal vessels of particular diameters is also important. Accurate application of pressure is important to oppose the walls of the vessel, to reduce the tissue impedance to a low enough value that allows enough electrosurgical energy through the tissue, to overcome the forces of expansion during tissue heating, and to contribute to the end tissue thickness which is an indication of a good seal. If the pressure is not great enough, the vessel may not properly or effectively seal and if the pressure is too great, the seal may shred or tear. It has been found that the amount of force required to produce an effective seal is at least partly dependent on the size and composition of the tissue to be sealed. Therefore, in order to help ensure an adequate seal, it would be advantageous to initially determine the size and/or composition of the tissue to be sealed and then apply the appropriate seal pressure.

Accordingly, a study was conducted to determine how seal pressure and blood vessel size influence the quality of the seal produced, measured through burst pressure. Seal pressure refers to the force imparted to tissue disposed, for example, between opposing jaw members of a surgical forceps. Burst pressure is the pressure required to open, or burst, a previously sealed vessel by forcing a fluid through the sealed vessel. The study was designed using a central composite response surface, a well known Design of Experiments (DoE) variation. The DoE contained two factors: seal pressure and vessel size. The range of values tested for seal pressure was 40 psi to 120 psi, while the vessel diameters ranged from 2 mm to 6 mm.

In testing, porcine renal arteries were removed and dissected and the diameter of the vessel was measured. The vessel was then placed on a research tool used for electrothermal bipolar vessel sealing. The pressure between the jaw members was set on the research tool to correspond with the appropriate seal pressure dictated by the DoE. A vessel seal was produced by applying bipolar energy to the seal plates using a ForceTriad™ generator manufactured by Valleylab (now Covidien Energy-based Devices) of Boulder, Colo. Once the seal was made, the vessel was held in place while water was pumped through the vessel for burst testing. A pressure calibrator was used to determine the maximum pressure the vessel could withstand prior to bursting. The burst pressures for all of the vessel sizes and pressure combinations were input into a statistical software package for further analysis. An Analysis of Variation (ANOVA) evaluation revealed that both vessel size and seal pressure were significant factors in determining the burst pressure (quality) of the resultant seal.

SUMMARY

In accordance with the present disclosure, a surgical forceps is provided. The forceps includes a housing and one or more shafts attached to the housing. An end effector assembly is disposed at a distal end of the shaft(s). The end effector assembly includes first and second jaw members disposed in opposing relation relative to one another. One or both of the jaw members is moveable from an open position to a closed position for grasping tissue. The jaw members include one or more sensing components that determine an output of cross-sectional diameter and/or composition of tissue disposed between the jaw members. A processing component is configured to receive the output from the sensing components and determine a seal pressure for adequately sealing tissue based upon the output. A regulating component, in communication with the processing component, is configured to regulate the movement of the jaw members such that upon movement from the open to the closed position, the determined seal pressure is applied to tissue disposed between the jaw members.

In one embodiment, the sensing component includes a pair of electrodes disposed through each of the jaw members. The electrodes are configured to pass an electrical signal through tissue disposed between the jaw members. The electrodes can thereby measure one or more electrical characteristics of tissue and determine the cross-sectional diameter and/or the composition of tissue. In one embodiment, the electrodes are configured to measure the impedance through tissue.

In another embodiment, the processing component includes an electrical circuit configured to receive the output from the sensing component and determine a seal pressure corresponding to that output.

In yet another embodiment, a generator, in communication with the processing component is provided. The generator is configured to store user-input data and use that data to, in conjunction with the processing component, determine a seal pressure corresponding to the output from the sensing component.

In still yet another embodiment, the regulating component includes a mechanically-driven system, an electrically-driven system and/or an electro-mechanically-driven system to regulate the seal pressure between the jaw members.

In yet another embodiment, the seal pressure determined by the processing component is a minimum seal pressure required to adequately seal tissue according to the output.

In another embodiment, the seal pressure determined by the processing component is a range of seal pressures for adequately sealing tissue according to the output.

A method of sealing tissue is also provided in accordance with the present disclosure. The method includes providing a surgical forceps having first and second jaw members disposed in opposing relation relative to one another. One or both of the jaw members are moveable from an open position to a closed position for grasping tissue. The method also includes the steps of determining a cross-sectional diameter and/or a composition of tissue disposed between the jaw members, determining a seal pressure for adequately sealing tissue according to the cross-sectional diameter and/or composition, and regulating the movement of the jaw members. The movement of the jaw members is regulated such that upon movement from the open to the closed position, the seal pressure is applied to tissue disposed the jaw members.

In another embodiment, the determined seal pressure is a minimum seal pressure required to adequately seal tissue.

In yet another embodiment, the determined seal pressure is a range of seal pressures for adequately sealing tissue.

BRIEF DESCRIPTION OF THE DRAWINGS

Various embodiments of the subject instrument are described herein with reference to the drawings wherein.

DETAILED DESCRIPTION

Figure 1:
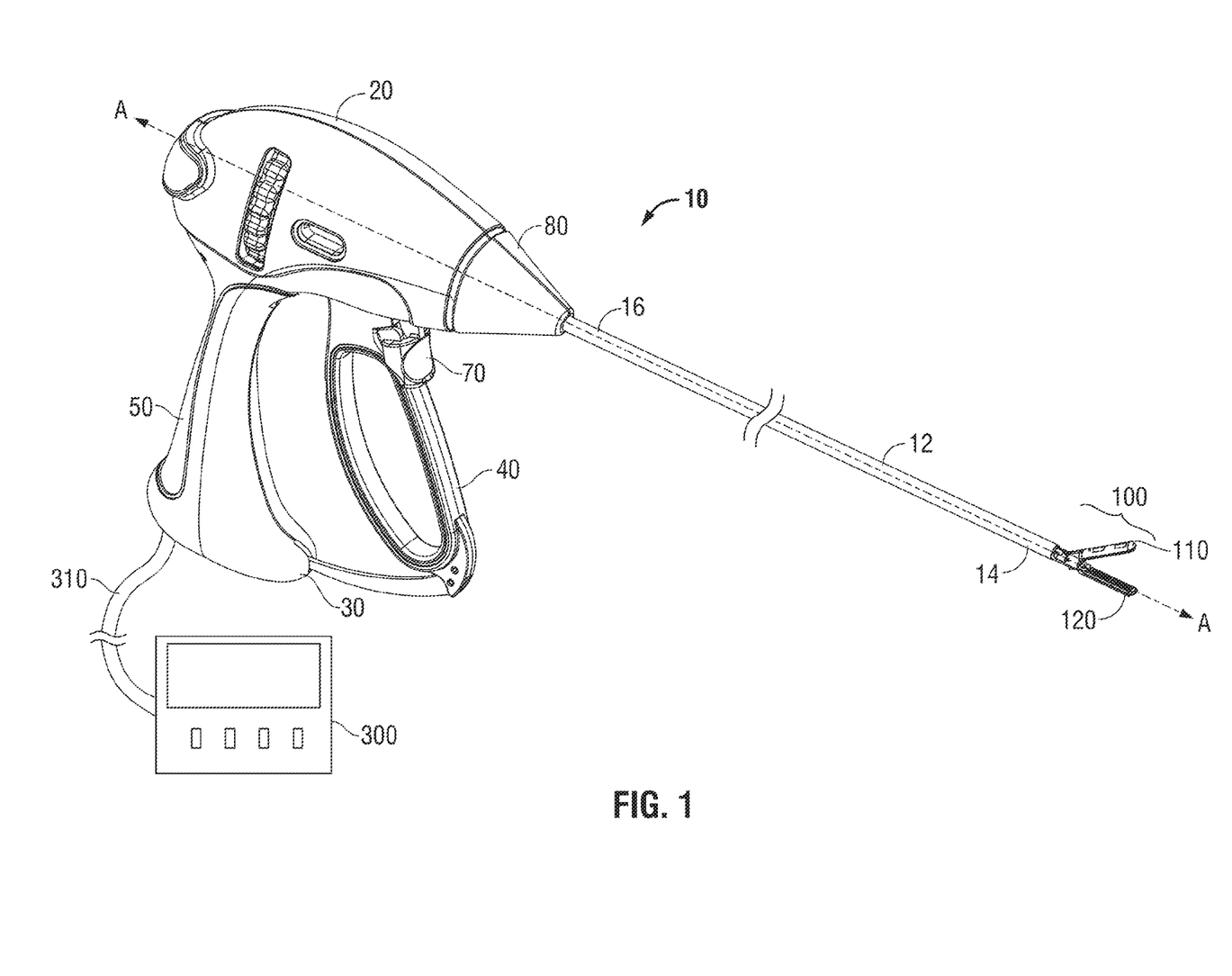
FIG. 1 is a top, perspective view of a surgical forceps including a housing, a handle assembly, a shaft, and an end effector assembly, for use with the present disclosure.

Turning now to FIG. 1, an endoscopic forceps 10 is shown that includes a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Forceps 10 also includes electro-surgical cable 310 that connects forceps 10 to a generator 300. Cable 310 has sufficient length to extend through shaft 12 in order to provide electrical energy to at least one of jaw members 110 and 120 of end effector assembly 100.

With continued reference to FIG. 1, rotating assembly 80 is integrally associated with housing 20 and is rotatable approximately 180 degrees in either direction about a longitudinal axis "A." The housing 20 includes two halves that house the internal working components of the forceps 10. Handle assembly 30 includes a moveable handle 40 and a fixed handle 50. Fixed handle 50 is integrally associated with housing 20 and handle 40 is moveable relative to fixed handle 50 in the direction of arrow "B" (see FIG. 3).

Figure 2:
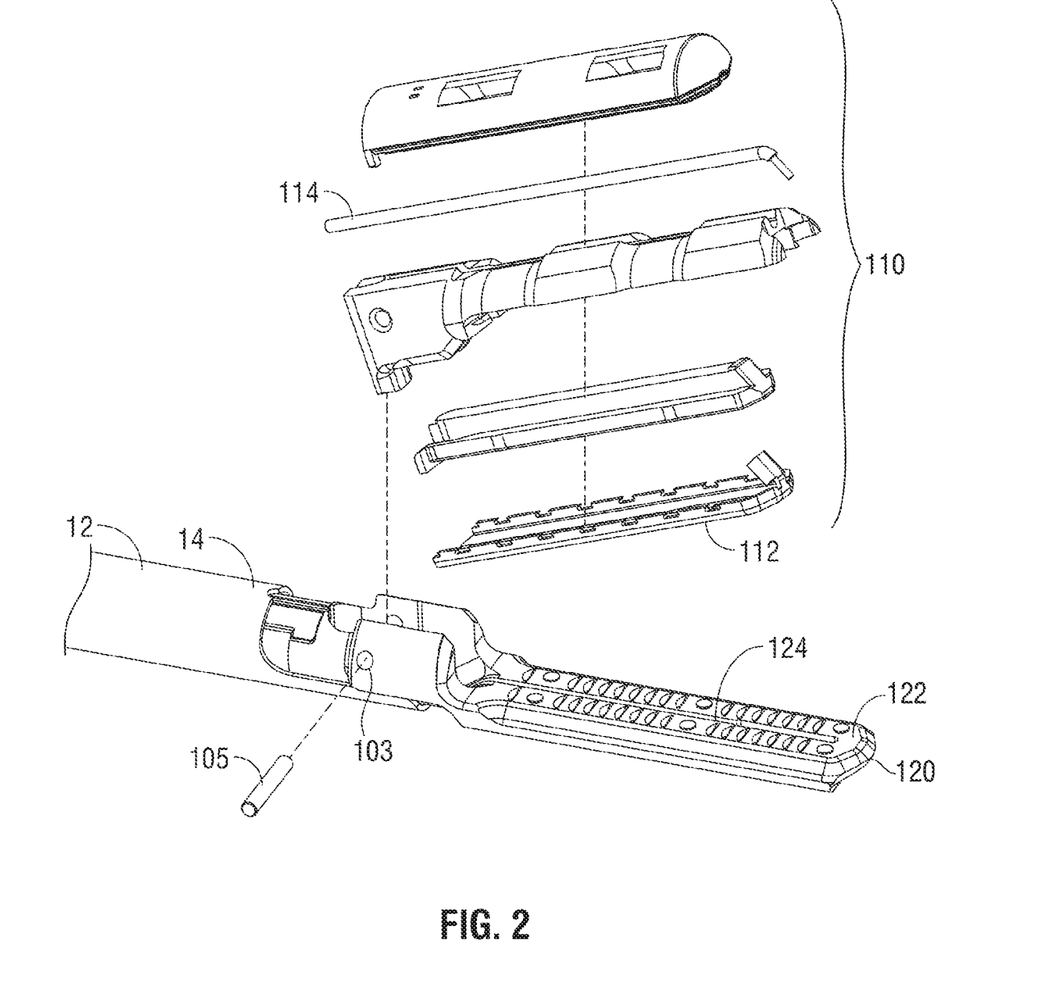
FIG. 2 is a enlarged, side, perspective view of the end effector assembly of FIG. 1, wherein the top jaw is shown with parts separated.

Referring now to FIG. 2, end effector assembly 100 is configured for mechanical attachment at the distal end 14 of shaft 12 of forceps 10. End effector assembly 100 includes a pair of opposing jaw members 110 and 120. Handle 40 of forceps 10 (see FIG. 1) ultimately connects to a drive assembly (not shown) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween.

With continued reference to FIG. 2, opposing jaw members 110 and 120 are pivotably connected about pivot 103 via pivot pin 105. Jaw members 110 and 120 include electrically conductive sealing plates 112 and 122 that are dimensioned to securely engage tissue when clamped therebetween. Each of the jaw members 110 and 120 also include a sensing component, or electrode pair 114 and 124, respectively, disposed therethrough. The electrode pairs 114 and 124 cooperate to measure the impedance across tissue disposed between the jaw members 110 and 120. Electrode pair 114 of jaw member 110, for example, may be configured to transmit a low-voltage alternating-current through tissue disposed between the jaw members 110 and 120, while electrode pair 124 of jaw member 120 may be configured to receive the resulting voltage after it has passed through tissue. It is also envisioned that this configuration may be reversed, e.g., where the transmitting electrodes are disposed through jaw member 120 and where the receiving electrodes are disposed through jaw member 110. In either configuration, the impedance across the tissue can be measured and used to determine the cross-sectional diameter of the tissue. Alternatively, the impedance across the tissue measured by the pairs of electrodes 114 and 124 can be used to determine the resistivity of the tissue. Since different components of tissue, e.g., muscle cells, fat cells and fluid, have different resistivities, determining the overall resistivity of the tissue can help determine the relative composition of the tissue. Further, a second pair of electrodes (not shown) or sensors may be disposed through each of the jaw members 110 and 120 such that the first set of electrode pairs 114 and 124 may be configured to measure the cross-sectional diameter of the tissue while the second set of electrode pairs is configured to measure the resistivity of the tissue.

It is also envisioned that any other suitable impedance sensing component may be provided in cooperation with jaw members 110 and 120 to measure the cross-sectional diameter and/or to determine the composition of tissue disposed between jaw members 110 and 120. Further, it is envisioned that the sensing component could include sensors disposed along the sealing plates 112 and 122 of jaw members 110 and 120, respectively, for sensing the gap distance between the respective sealing plates 112 and 122. By determining the gap distance between the sealing plates 112 and 122 at different positions along the plates, the size of the vessel grasped therebetween can be estimated.

Ultimately, the sensing component may be configured to measure any electrical or physical characteristic of tissue that may be used to determine a diameter of tissue or tissue composition. Accordingly, any sensor that may be used to measure an electrical or physical characteristic of tissue may be provided for use with end effector assembly 100 of forceps 10. Suitable sensors include, but are not limited to, impedance sensors, proximity sensors, optical sensors, ultrasonic sensors, chemical sensors, and the like.

Figure 3:
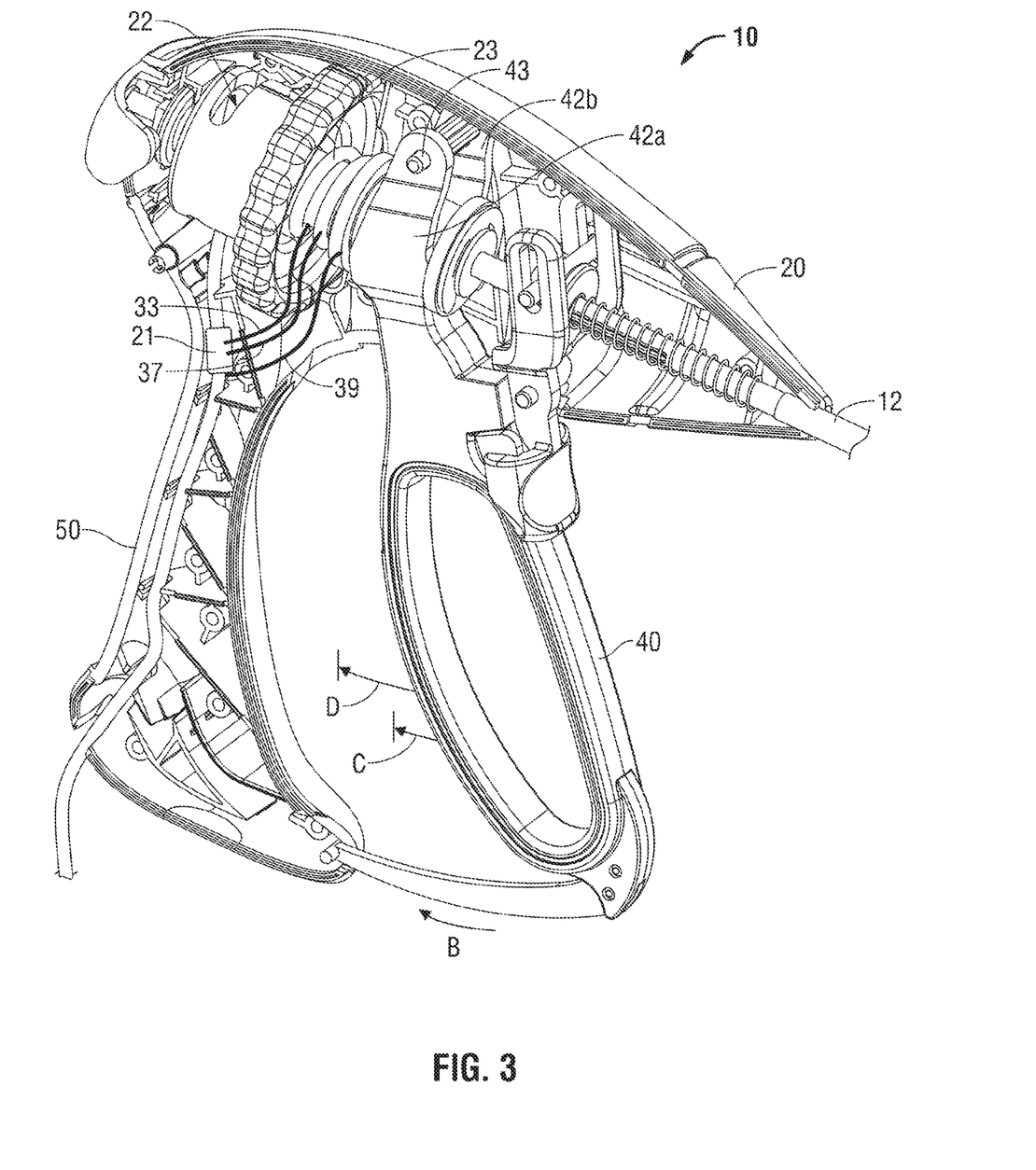
FIG. 3 is a side, perspective view of the housing of the forceps of FIG. 1, with a half of the housing removed.

Referring now to FIG. 3, housing 20 of forceps 10 is shown having a half of housing 20 removed. A processing component 21, disposed within housing 20, is configured to receive an output, e.g., a cross-sectional diameter and/or a composition of tissue from the sensing component 114. One or more leads 33, 37 are disposed through the housing 20 and shaft 12 to the jaw members 110 and 120 to provide feedback to the processing component 21. The processing component 21 converts the output into a seal pressure according to specific the characteristics, e.g., the cross-sectional diameter and/or the composition, of the tissue to be sealed. It is envisioned that the processing component 21 may determine the minimum seal pressure required to adequately seal the tissue disposed between the jaw members 110 and 120. Alternatively, the processing component 21 may be configured to determine a seal pressure range for sealing tissue disposed between the jaw member 110 and 120.

The processing component 21 includes electrical circuitry 22 configured to convert the output into a seal pressure, or seal pressure range, for adequately sealing tissue disposed between the jaw members 110 and 120. Electrical circuitry 22 may be configured to convert the output to a seal pressure according to specific parameters and/or data. Alternatively, electrical circuitry 22 may communicate with an external source, e.g. generator 300, for determining the seal pressure corresponding to the tissue cross-sectional diameter and/or composition. Further, a computer chip (not shown) may be provided for storing data and communicating with the electrical circuitry 22 in order to determine the appropriate seal pressure, or seal pressure range, based upon the output from the sensing component 114. Specific data sets, e.g., the set of minimum seal pressures required for adequate sealing of vessels having varying cross-sectional diameters, may be used to convert the output cross-sectional diameter into a seal pressure. Algorithms can also be used to determine the seal pressure based upon the specific output. Exemplary data, determined by a study of seal pressure as a function of vessel size, for configuring the processing component 21, will be discussed in detail below.

With continued reference to FIG. 3, a regulating component 23 is shown in communication with the processing component 21 via lead 39. Regulating component 23 regulates movement of the jaw members 110 and 120 such that the determined seal pressure, or seal pressure range, is imparted to tissue disposed therebetween. Regulating component 23 may be an electro-mechanical component or a mechanical component, e.g., a system of gears 23, configured to define a specific range of motion of moveable handle 40 with respect to fixed handle 50. In such an embodiment, regulating component 23 would operate to limit the displacement of tabs 42a and 42b about pivot 43, thereby limiting the movement of moveable handle 40 with respect to fixed handle 50. Accordingly, a user would be prevented from squeezing handle 40 beyond a certain point. For example, if the determined seal pressure required to seal tissue disposed between jaw members 110 and 120 was relatively small, regulating component 23 would operate to prevent handle 40 from moving past position "C." However, if the determined seal pressure were larger, regulating component 23 would operate to allow handle 40 to be moveable to position "D." The movement of handle 40 to specific positions, e.g., position "C" or position "D," corresponds to a specific seal pressure imparted to tissue, since handle 40 and drive assembly (not shown) cooperate to impart movement of the jaw members 110 and 120 from the open to the closed position. Therefore, defining a specific range of motion of handle 40 allows the determined seal pressure (corresponding to the fully squeezed position, e.g., position "C" or position "D") to be applied to tissue disposed between jaw members 110 and 120. Accordingly, a user need not selectively squeeze handle 40 to approximate the proper seal pressure, but may squeeze handle 40 through its allowed range of motion (as defined by regulating component 23), thereby imparting the proper seal pressure to tissue disposed between jaw member 110 and 120.

As can be appreciated, the specific range of motion of handle 40 is determined by the seal pressure communicated to the regulating component 23 by the processing component 21. Alternatively, regulating component 23 may be electro-mechanically operated but may be configured to function in a similar manner. Further, any suitable regulating component capable of regulating movement of the jaw members 110 and 120 according to a determined seal pressure or seal pressure range, may be used in accordance with the present disclosure.

Figure 4:
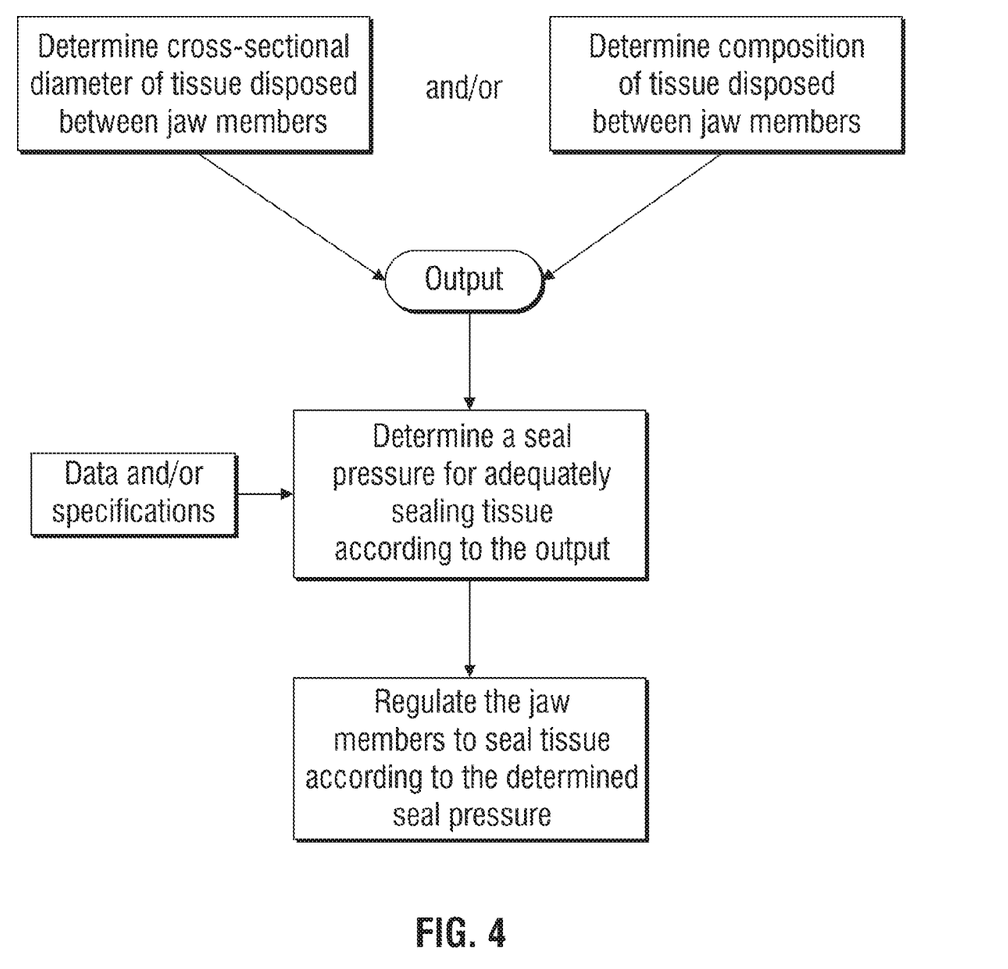
FIG. 4 is flow chart illustrating a method of sealing tissue in accordance with the present disclosure.

With reference now to FIG. 4, a method of sealing tissue is shown for use with forceps 10. First, a cross-sectional diameter and/or composition of tissue disposed through jaw members 110 and 120 of a forceps 10 is determined as an output. The output is then used to determine a seal pressure required for adequately sealing tissue according to predetermined data and/or specifications. The determined seal pressure is then used to regulate the movement of the jaw members 110 and 120 such that the determined seal pressure is applied to tissue between jaw member 110 and 120 to thereby effectively seal tissue disposed therebetween.

As mentioned above, specific data may be input into the processing component 21 to determine the appropriate seal pressure corresponding to the specific tissue cross-sectional diameter and/or composition. In the study discussed above, vessels having diameters ranging from 2 mm to 6 mm were sealed by applying seal pressures ranging from 40 psi to 120 psi. Table 1, below, shows the results of the above-mentioned study, wherein the seal pressures indicated refer to the minimum seal pressure required to affect an adequate seal. The exemplary data represented in FIG. 1 corresponds to seal plate 112 and 122 (see FIG. 2) widths of 0.083 inches.

| VESSEL DIAMETER (mm) | MINIMUM SEAL PRESSURE (psi) |
| --- | --- |
| 2 | 41 |
| 3 | 30 |
| 4 | 37 |
| 5 | 60 |
| 6 | 103 |

Figure 5:
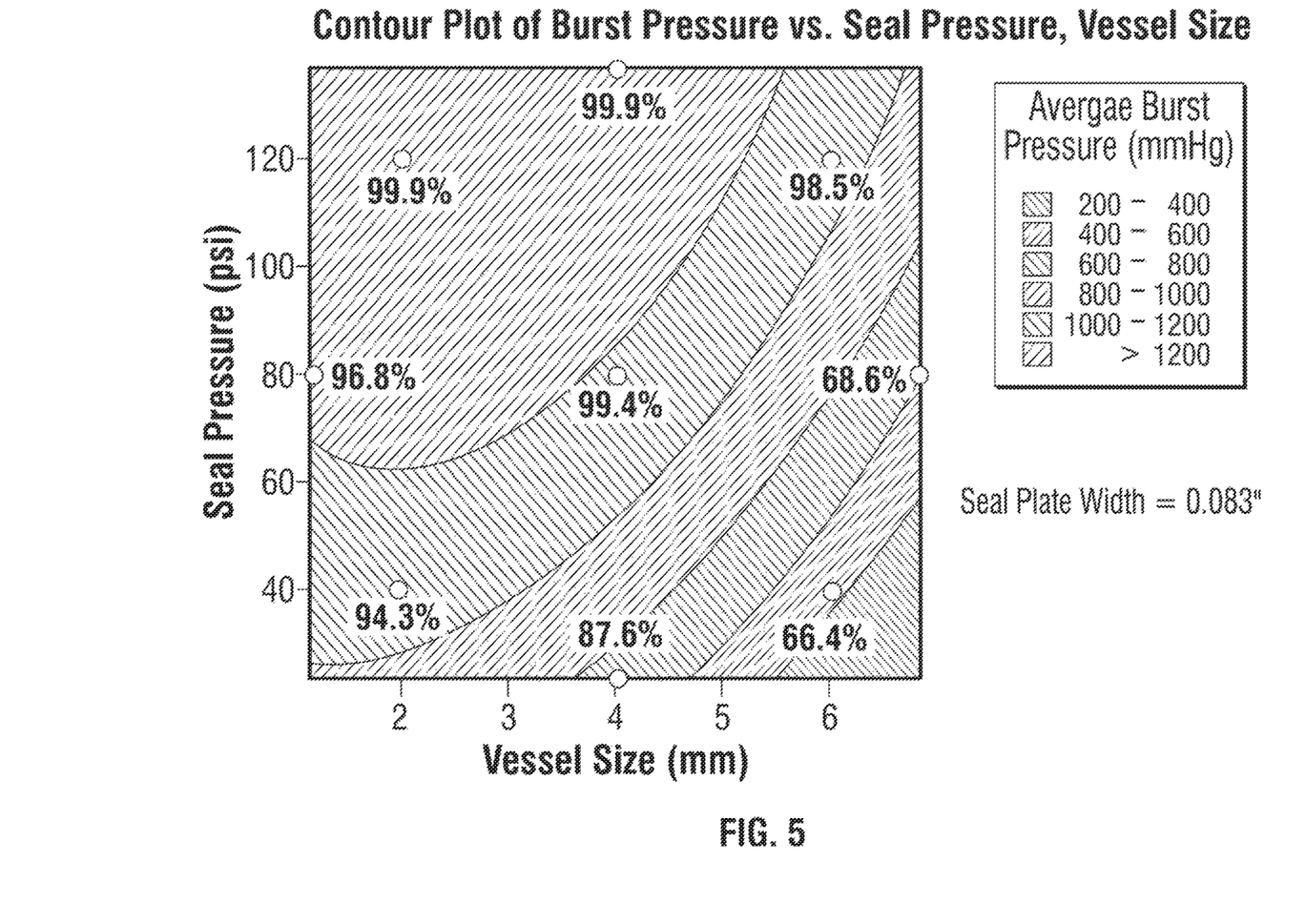
FIG. 5 is a contour plot of mean burst pressure as a result of seal pressure and vessel size with 0.083 inch wide seal plates.

The minimum seal pressure was determined as the seal pressure required to produce a seal having a 98.5% probability of a burst pressure greater than 360 mmHg. However, depending on the vessel or tissue to be sealed, a greater (or smaller) burst pressure may be desired to ensure proper sealing. As such, the data would need to be altered accordingly. FIG. 5 shows the contour plot of the mean burst pressure as a result of seal pressure and vessel size with 0.083 inch wide seal plates 112 and 122. The points on the plot represent the probability of a burst pressure greater than 360 mmHg according to the specific vessel size and seal pressure tested.

As mentioned above, this data may be used in conjunction with processing component 21 of forceps 10 having seal plates 112 and 122 of 0.083 inch widths, to determine the proper seal pressure to apply to a vessel having a given cross-sectional diameter. For example, end effector assembly 100 of forceps 10 may be positioned such that a vessel is disposed between jaw members 110 and 120. The sensing component 114 may then determine that the cross-sectional diameter of the vessel is, for example, 6 mm. This output, e.g., a 6 mm cross-sectional diameter, would then be communicated to the processing component 21. If the processing component 21 was configured with the data from Table 1, above, the processing component 21 would determine that a minimum seal pressure of 120 psi would be required to effectively seal the 6 mm vessel disposed between the jaw members 110 and 120. Accordingly, the regulating component 23 would regulate the movement of the jaw members 110 and 120 such that when handle 40 is squeezed, thereby closing jaw members 110 and 120, a seal pressure of 120 psi is applied to seal the vessel disposed between jaw members 110 and 120. Thus, the user can be confident that the tissue seal created has approximately a 98.5% probability of a burst pressure greater than 360 mmHg. As can be appreciated, the input data can be adjusted to achieve a higher, or lower, seal quality probability.

Table 2, below, shows the results of the above-mentioned study, wherein the seal plate 112 and 122 widths are 0.029 inches.

| VESSEL DIAMETER (mm) | MINIMUM SEAL PRESSURE (psi) |
| --- | --- |
| 2 | <23 |
| 3 | 33 |
| 4 | 33 |
| 5 | 54 |
| 6 | 92 |

Figure 6:
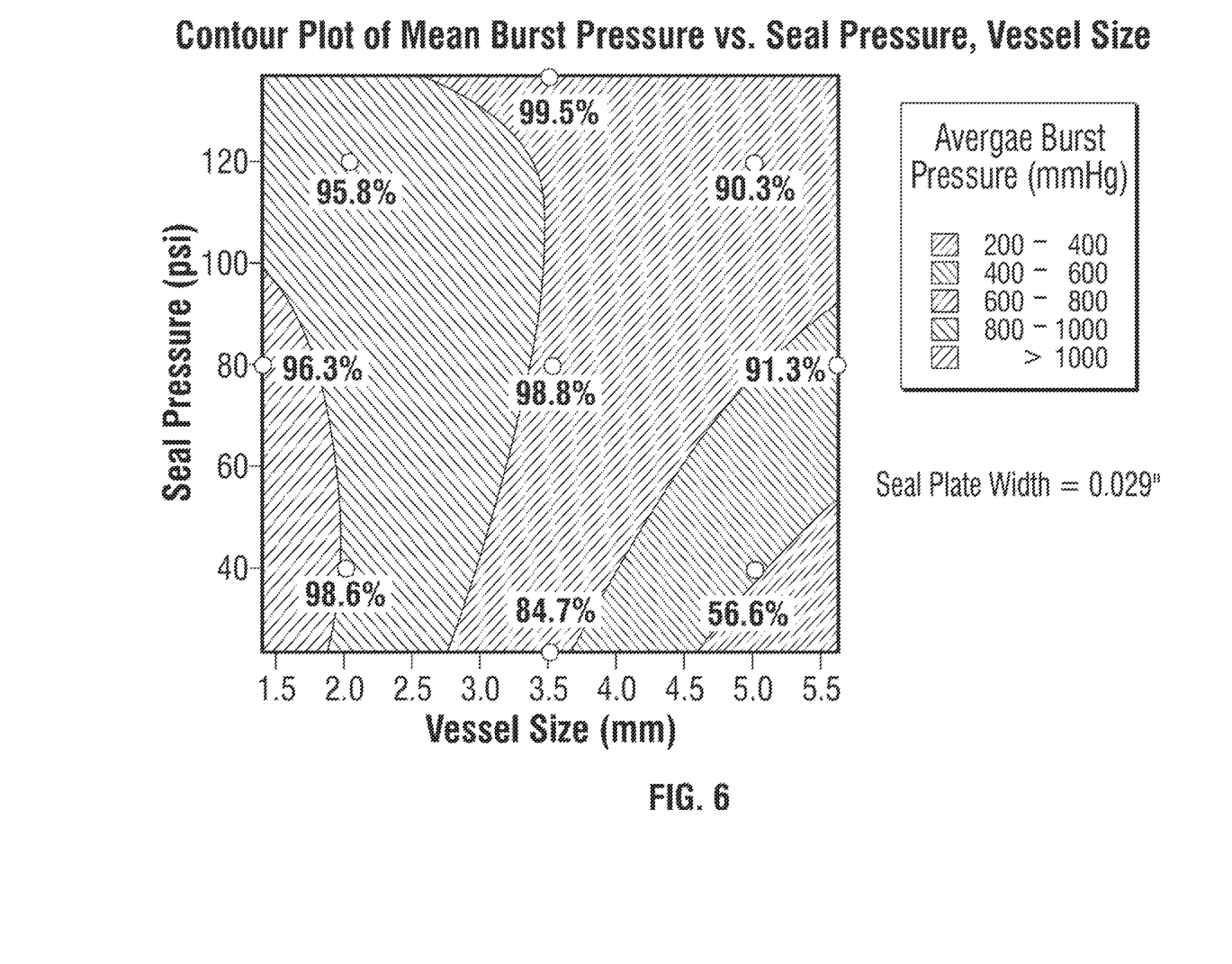
FIG. 6 is a contour plot of the mean burst pressure as a result of seal pressure and vessel size with 0.029 inch wide seal plates.

As with Table 1, the minimum seal pressures in Table 2 were determined as the seal pressure required to produce a seal having a 98.5% probability of a burst pressure greater than 360 mmHg. FIG. 6, corresponding to the data of Table 2, shows the contour plot of the mean burst pressure as a result of seal pressure and vessel size with 0.029 inch wide seal plates 112 and 122. As with the data from Table 1, this data may be used in conjunction with processing component 21 of forceps 10 having seal plates 112 and 122 of 0.029 inch widths, to determine the proper seal pressure to apply to a vessel having a given cross-sectional diameter.

As described above, the minimum seal pressures required to adequately seal vessels having a given diameter shown in Table 1 and Table 2, above, may be input into the processing component 21. Thus, in operation, as jaw member 110 and 120 of forceps 10 are moved to the closed position with tissue grasped therebetween, regulating component 23 ensures that the minimum seal pressure is applied to tissue, thereby helping to ensure an effective seal. Regulating component 23 also helps prevent tissue damage as a result of too much pressure being applied by preventing excess pressure from being applied to the tissue. Further, the contour plots of FIGS. 5 and 6 may be used to define a seal pressure range according to the vessel cross-sectional diameter determined by the sensing components 114 and 124.

Determining a minimum seal pressure is also useful in the design and manufacturing of forceps, such as forceps 10. Knowing the minimum amount of pressure needed to seal a vessel having a particular diameter provides a designer with a specific seal pressure the device must be able to achieve. For example, if a given forceps 10 is to be designed for use with vessels ranging from 2 mm to 6 mm, the designer must create a forceps having a seal pressure capable of reaching the minimum seal pressure required for a 6 mm vessel. However, the designer need not create a forceps capable of achieving a higher seal pressure. Knowing the actual force required for a given vessel size allows the designer to avoid unnecessary constraints while designing the forceps. This is especially useful when designing forceps for use in laparoscopic and/or NOTES procedures, since it is difficult to achieve high seal pressures with relatively small jaw members.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
an end effector assembly including first and second jaw members each including a sealing surface, at least one of the first or second jaw members movable relative to the other to grasp tissue between the sealing surfaces, at least one of the first or second jaw members including a sensor configured to determine a cross-sectional diameter of a tissue grasped between the sealing surfaces by measuring an impedance across the tissue grasped between the sealing surfaces or at least one property of the tissue grasped between the sealing surfaces and determine an output based upon the cross-sectional diameter of the tissue or the at least one property;
a processor configured to receive the output from the sensor and determine a seal pressure for adequately sealing the tissue grasped between the sealing surfaces based upon the output; and
a regulator in communication with the processor and configured to receive the determined seal pressure from the processor, the regulator configured, based on the determined seal pressure received, to regulate movement of the at least one of the first or second jaw members such that the first and second jaw members apply the determined seal pressure to the tissue grasped between the sealing surfaces.

2. The electrosurgical system according to claim 1, wherein the sealing surfaces of the first and second jaw members are configured to pass an electrical signal through the tissue to measure an electrical characteristic therethrough to thereby determine the at least one property.

3. The electrosurgical system according to claim 2, wherein the electrical characteristic is impedance.

4. The electrosurgical system according to claim 1, wherein the at least one property is a composition of the tissue.

5. The electrosurgical system according to claim 1, wherein the regulator includes at least one of a mechanically-driven system, an electrically-driven system, or an electro-mechanically-driven system.

6. The electrosurgical system according to claim 1, wherein the determined seal pressure is a minimum seal pressure required to adequately seal tissue according to the output and the width.

7. The electrosurgical system according to claim 1, wherein the processor is associated with an electrosurgical generator configured to determine the seal pressure.

8. The electrosurgical system according to claim 7, further comprising a chip storing data indicating the width.

9. The electrosurgical system according to claim 8, wherein the chip is disposed within a housing, and wherein the end effector assembly is coupled to and distally-spaced from the housing.

10. The electrosurgical system according to claim 9, wherein the housing includes a movable handle associated therewith and configured to manipulate the end effector assembly.

11. The electrosurgical system according to claim 9, wherein the data indicating the width is configured to be communicated from the chip to the electrosurgical generator.

12. The electrosurgical system according to claim 1, wherein the processor is disposed within a housing, and wherein the end effector assembly is coupled to and distally-spaced from the housing.

13. The electrosurgical system according to claim 1, wherein the sensor includes at least one of: a proximity sensor, an optical sensor, an ultrasonic sensor, or a chemical sensor.

14. The electrosurgical system according to claim 1, wherein adequately sealed tissue is tissue having a 98.5% probability of burst pressure greater than 360 mm Hg.

15. An electrosurgical system, comprising:
an end effector assembly including first and second jaw members each including a sealing surface, at least one of the first or second jaw members movable relative to the other to grasp tissue between the sealing surfaces, at least one of the first or second jaw members including a sensor configured to determine a cross-sectional diameter of a tissue grasped between the sealing surfaces or a composition of the tissue grasped between the sealing surfaces by measuring an impedance across the tissue grasped between the sealing surfaces and determine an output based upon the cross-sectional diameter of the tissue or the composition of the tissue;
a processor configured to receive the output from the sensor and determine a seal pressure for adequately sealing the tissue grasped between the sealing surfaces based upon the output; and
a regulator in communication with the processor and configured to receive the determined seal pressure from the processor, the regulator configured, based on the determined seal pressure received, to regulate movement of the at least one of the first or second jaw members such that the first and second jaw members apply the determined seal pressure to the tissue grasped between the sealing surfaces.

16. The electrosurgical system of claim 15, wherein the sensor is further configured to measure the resistivity of the tissue grasped between the sealing surfaces to determine the composition of the tissue.

17. The electrosurgical system according to claim 15, wherein the sensor includes at least one of: a proximity sensor, an optical sensor, an ultrasonic sensor, or a chemical sensor.

\* \* \* \* \*